United States Patent [19]

Statham

[11] Patent Number: 5,357,110
[45] Date of Patent: Oct. 18, 1994

[54] VISUAL COLOR MAPPING X-RAY ANALYSIS APPARATUS

[75] Inventor: Peter J. Statham, High Wycombe, England

[73] Assignee: Link Analytical Limited, Witney, England

[21] Appl. No.: 48,387

[22] Filed: Apr. 16, 1993

[30] Foreign Application Priority Data

May 1, 1992 [GB] United Kingdom ............ 9209500

[51] Int. Cl.$^5$ ............................................. H01J 37/00
[52] U.S. Cl. .................................... 250/307; 250/310
[58] Field of Search ............... 250/310, 311, 396 R, 250/397, 398, 306, 307; 378/100

[56] References Cited

U.S. PATENT DOCUMENTS

| | | | |
|---|---|---|---|
| 2,982,814 | 5/1961 | Fine et al. | 178/6.8 |
| 3,812,288 | 5/1974 | Walsh et al. | 250/310 |
| 4,439,680 | 3/1984 | Broadhurst | 250/310 |
| 4,857,731 | 8/1989 | Tagata | 250/310 |
| 5,212,383 | 5/1993 | Scharf | 250/310 |

OTHER PUBLICATIONS

R. S. Dhariwal, J. A. McClean, I. M. Hjelmfoss, "Three–Colour X–Ray Mapping Using Digital Storage", *Scanning*, vol. 11, 1989, pp. 73–79.
G. DiGiacomo and J. Ordonez, "Electron Microprobe Analysis Through Colorimetry", IBM Technical Disclosure Bulletin, vol. 14, No. 1, Jun. 1971, pp. 165–166.
G. DiGiacomo and J. Ordonez, "Colorimetry Applied to Quantitative Chemical Analysis in Electron Probe Microanalysis", IBM Technical Disclosure Bulletin, vol. 13, No. 11, Apr. 1971, pp. 3198.
Patent Abstract of Japan, No. 58-190716; Nov. 1983.
Patent Abstract of Japan, No. 61-62849; Mar. 1986.
Patent Abstract of Japan, No. 61-62850; Mar. 1986.
Patent Abstract of Japan, 57-36762; Feb. 1982.

*Primary Examiner*—Jack I. Berman
*Assistant Examiner*—James Beyer
*Attorney, Agent, or Firm*—Cooper & Dunham

[57] ABSTRACT

Apparatus for displaying a visual image of the X-ray response of a specimen comprises an electron beam source for exciting X-ray emissions from the specimen. A detector detects X-ray photons emitted by the specimen and generates output signals representing the energies of X-ray photons received from discrete pixels of the specimen in a plurality of energy bands. A set of look-up tables generate for each pixel and for each energy band visual colour component signals related to the mean energy of X-ray photons emitted from the pixel and detected by the detector in that energy band. The range of X-ray energies is mapped into a range of visual colours. An accumulator combines the colour component signals for each pixel. The colour components for each pixel are stored in a frame store which is connected to a monitor which displays an image defined by the colour components.

16 Claims, 3 Drawing Sheets

VISUAL COLOR MAPPING X-RAY ANALYSIS APPARATUS

FIELD OF THE INVENTION

The invention relates to apparatus and methods for displaying a visual image of the X-ray response of a specimen.

DESCRIPTION OF THE PRIOR ART

There is a well-established technique for acquiring digital X-ray images. This involves directing an electron beam over a grid of points on a specimen surface. At each grid point, an X-ray energy spectrum is acquired and data are extracted from this spectrum for selected chemical elements of interest. In the simplest case, these data consist of say N integrals of counts recorded in energy bands (or "windows") surrounding the characteristic energy for each element of concern but more sophisticated techniques have been used to extract the area of each characteristic peak above background and hence the characteristic line intensity for the element of interest. Each data value is used as the "pixel" intensity at that grid point for the element of concern so, after scanning over all the grid points covering the field of view, a set of N digital images corresponding to the N chemical elements of interest is obtained.

These images are commonly referred to as "X-ray maps" and are commonly displayed using a computer monitor using a separate colour or hue for each element. For example, the "silicon" map could be displayed in yellow, the "iron" map in red, the "titanium" map in green etc. An example of such a system is described in US-A-4857731.

Images have also been combined by processing to show where certain elements co-exist in regions of a specimen. That is, once the original X-ray map data have been acquired, the images are inspected (either by the user, or by some automatic mathematical technique such as principal component analysis) and then recombined in suitable combinations to reveal the distribution of phases in the specimen (where each phase consists of elements occurring in specific ratios and is shown in a suitable colour).

Information presented in this conventional way has to be interpreted by skilled operators who can recognise the special colours and manipulate the N digital images in the correct manner. Furthermore, systems which convert a single signal to false colour cannot distinguish between different compositions which produce the same signal intensity.

U.S. Pat. No. 4439680 describes a system in which detected X-ray energy is converted to electrical pulses, the height of which is proportional to the detected X-ray energy. The pulse signals are coded so as to trigger or energise the guns of a conventional colour cathode ray tube. This system achieves "real-time" display but requires that the X-ray energy pulses be converted to hue and displayed "on the fly", at the speed of a conventional TV scan. X-ray photons arrive with a random (Poisson) time distribution so that "pile up" in the spectrometer can occur before each photon is measured. Intensity information is distorted if the beam moves significantly during the time it takes to measure a single photon which is typically several to tens of microseconds with a Si(Li) detection system. Furthermore, measured photon rates are invariably low (<100 kHz) so images will only be scattered "dots" if the average number of photons per pixel is less than one. Thus, a live TV-rate scan (roughly 0.1 microseconds per pixel) gives a very noisy X-ray image with the potential for substantial intensity distortion.

SUMMARY OF THE INVENTION

In accordance with one aspect of the present invention, apparatus for displaying a visual image of the X-ray response of a specimen comprises means for exciting X-ray emissions from a specimen; detection means for detecting X-ray photons emitted by the specimen; visual colour component generating means for generating for each pixel sets of visual colour component signals related to the energies of x-ray photons emitted from the pixel and detected by the detector, wherein the range of detected X-ray energies is mapped into a range of visual colours; accumulator means for combining the respective colour component signals for each pixel into a single set of colour components for the pixel; and display means responsive to the colour component signals from the accumulator means to display an image defined by the colour components.

In accordance with a second aspect of the present invention, a method of displaying a visual image of the X-ray response of a specimen comprises exciting X-ray emissions from a specimen; detecting X-ray photons emitted by the specimen; generating for each pixel sets of visual colour component signals related to the energies of X-ray photons emitted from the pixel and detected by the detector wherein the range of detected X-ray energies is mapped into a range of visual colours; combining the respective colour component signals for each pixel into a single set of colour components for that pixel; and displaying an image defined by the resultant set of colour components.

With this invention, the X-ray spectrum, which is invisible to the human observer, is converted or mapped into the spectrum of visible colours. For example, long wavelengths (low energy) X-rays can be converted to red and higher energies are converted to the standard optical "rainbow" of colours so that the highest energy X-rays may appear in blue. By using accumulator means, it is possible to build up a representation of the range of energies of X-ray photons received from each pixel, these ranges then being individually mapped into the corresponding range of visual colours leading to a more useful display of the elements present in the specimen. The accumulator means allows us to dwell for as long as we like on a single pixel to accumulate sufficient X-ray data to get a clear estimate of compositional colour and also to make corrections for pile-up which will be accurate for that pixel.

Ideally, the detection means detects individual photons and outputs signals representing the energy of each photon, the visual colour component generating means generating a set of colour component signals for each photon.

In practice, however, the apparatus further comprises second accumulator means including an accumulator for each of a number of X-ray energy bands, each accumulator storing, during the period for which a pixel is scanned, the number of photons generated in the corresponding energy band, wherein the visual colour component generating means generates a set of colour component signals for each energy band scaled by the values stored in the respective accumulators.

Typically, the plurality of energy bands will be adjacent to one another although in some cases, these could be spaced apart (e.g. 1–3 keV, 4–5 keV, 6–10 keV).

It should be understood in this context that the term "energy" is used to refer to the energy of a single X-ray photon.

The resulting image defined by the colour component signals can be displayed in full colour on a display device such as a CRT and the image will display all the normal properties of real colour objects that human operators are used to seeing. In particular, objects which have the same chemical composition tend to have a characteristic colour which is independent of signal intensity. As with real colour objects, this characteristic colour is only slightly affected by surface topography and orientation of the sample. Objects with different chemical composition often show different colours. Thus, in a single image, the user can recognise areas likely to be of different chemical composition and no special sample preparation is required (as would be the case for other techniques for recognising compositional variations), while the selective combination of digital images by the user is avoided. Furthermore, the processing can be accomplished within the acquisition time for a single pixel so a continuously updating image can be viewed "real time".

Typically, the means for exciting X-ray emissions comprises a focused beam of electrons but other excitation means could be used, for example a micro-collimated X-ray beam or a focused photon beam. In practice, the beam would be scanned across the specimen in a step-wise manner so as to excite a response from discrete pixels, that response being processed as described resulting in a set of colour component control signals which are then used to generate a resultant colour for that pixel.

The detection means can comprise any conventional X-ray energy dispersive detector system such as the Link eXL or Link ISIS manufactured by Oxford Instruments, Microanalysis Group.

Depending upon the design of the detection means, the output signal generated by the detection means may represent the energy of an individual photon or the mean intensity for a restricted range of photon energies.

The visual colour component control signal generating means will typically comprise a mixture of hardware and software components. Typically, however, the visual colour component generating means includes one or more look-up tables (LUTs) which contain data defining the visual colour component control signal values corresponding to each X-ray energy value output by the detector or each mean energy band level.

The precise mapping between the X-ray energies and corresponding colour component intensities is not critical but is preferably arranged such that the resultant images show a realistic and reproducible colour effect and different compositions will present different visual colours in the displayed image.

A very general way of expressing the conversion from X-ray signals to colour is to say that the resultant colour vector $\underline{X}(X_r, X_g, X_b)$ is given by $$X = \text{Sum}_i(n_i \underline{C_i}) \qquad (1)$$

Where $n_i$ is proportional to the number of x-rays in energy band i, with mean energy $E_i$, which are detected in the total pixel dwell time, $\underline{C_i}$ is the colour vector (r,g,b components) which should be used for photons of energy $E_i$ and $\text{Sum}_i$ indicates the sum for all energy bands i detected.

One problem which often arises with X-ray imaging techniques is the very low data rate achieved. This means that the X-ray images obtained are very noisy (that is, the number of photons recorded varies abruptly from pixel to pixel even when the sample excitation, and thus mean intensity, is uniform). The noise can be reduced by averaging the results of many scans over the field of view, or by scanning very slowly and measuring and storing the average X-ray intensity at each picture element (pixel). However, it may take many minutes to acquire a good x-ray image so that the technology is not "interactive".

Another way of reducing the noise is to acquire a digital X-ray image and by computer processing, replace each pixel intensity with the average intensity for all pixels in a small region surrounding the pixel. Obviously, this has a "blurring" effect on the final image and the degree of blurring depends on both the method of averaging and the size of the region around each pixel. The more the image is blurred, the better the level of noise reduction so there is an effective limit on attainable resolution set by the degree of noise in the original data.

Preferably, the apparatus further comprises an auxiliary detector for detecting another characteristic of the specimen; and modifying means for modifying the colour component signals from the accumulator means so as to modify the luminance of each pixel while leaving the hue and saturation substantially unchanged.

This extension of the invention makes use of the fact that although the intensity information in the X-ray data is very noisy, the hue and saturation are usually determined with higher precision. This can be seen by considering a spectrum from a pure element where most X-rays emerge with the characteristic X-ray energy for that element; although we may accumulate only a few photons, n, in a small measurement interval so the statistical fluctuation ($n^{0.5}$) is large, photons of the same energy are converted to the same R,G,B result so the proportions of R,G,B which affect hue and saturation are the same, however long the acquisition interval. Furthermore, the human eye has more resolution sensitivity to intensity variation or luminance than to variations in hue and saturation or chromaticity.

Although the invention without this extension can be used to obtain a 128×128 pixel X-ray colour image in about 16 seconds, with the extension a 512×512 pixel image can be obtained in the same time.

Typically, the additional information is generated by monitoring backscattered electrons (BSED) or secondary electrons (SED) emitted by the specimen. These signals are used conventionally to generate high resolution images on electron microscopes and are of high resolution and relatively free of noise but are essentially monochrome. Other possibilities are SCD: Specimen current detector (measures absorbed specimen current); or transmitted electron detector (measures electrons that have passed through the sample).

Essentially, therefore, the preferred arrangements make use of the accumulated X-ray data at each pixel to determine the chromaticity (balance of red, green and blue) and uses the auxiliary signals such as an electron signal to determine the luminance of the pixel as displayed in the final image. Even if the image acquisition time is short, the colour content provided by the X-ray data will be sufficiently well resolved to "paint" the high resolution electron image in the appropriate colours. In general, the electron signal data would be acquired at the same time as the X-ray data. If greater scan speeds are required, the X-ray data can be obtained at fewer points than the electron signal data, the intervening points being determined by interpolation.

This preferred technique retains the advantage of the original in that compounds exhibit a characteristic colour, even though two compounds may fortuitously give the same colour.

The degree of colour content in the image could be left for the operator to adjust. At one extreme, the original b/w image of the electron signal would show the best possible resolution and no colour whatsoever. At the other extreme, the colour of a pixel would be completely determined by the X-ray data. In between, the operator would be effectively adjusting the degree of "saturation" of the available colour signal.

It will be appreciated that processing aspects of the invention can be implemented in hardware or software.

BRIEF DESCRIPTION OF THE DRAWINGS

Examples of apparatus according to the invention will now be described with reference to the accompanying drawings, in which.

EMBODIMENT

Figure 1:
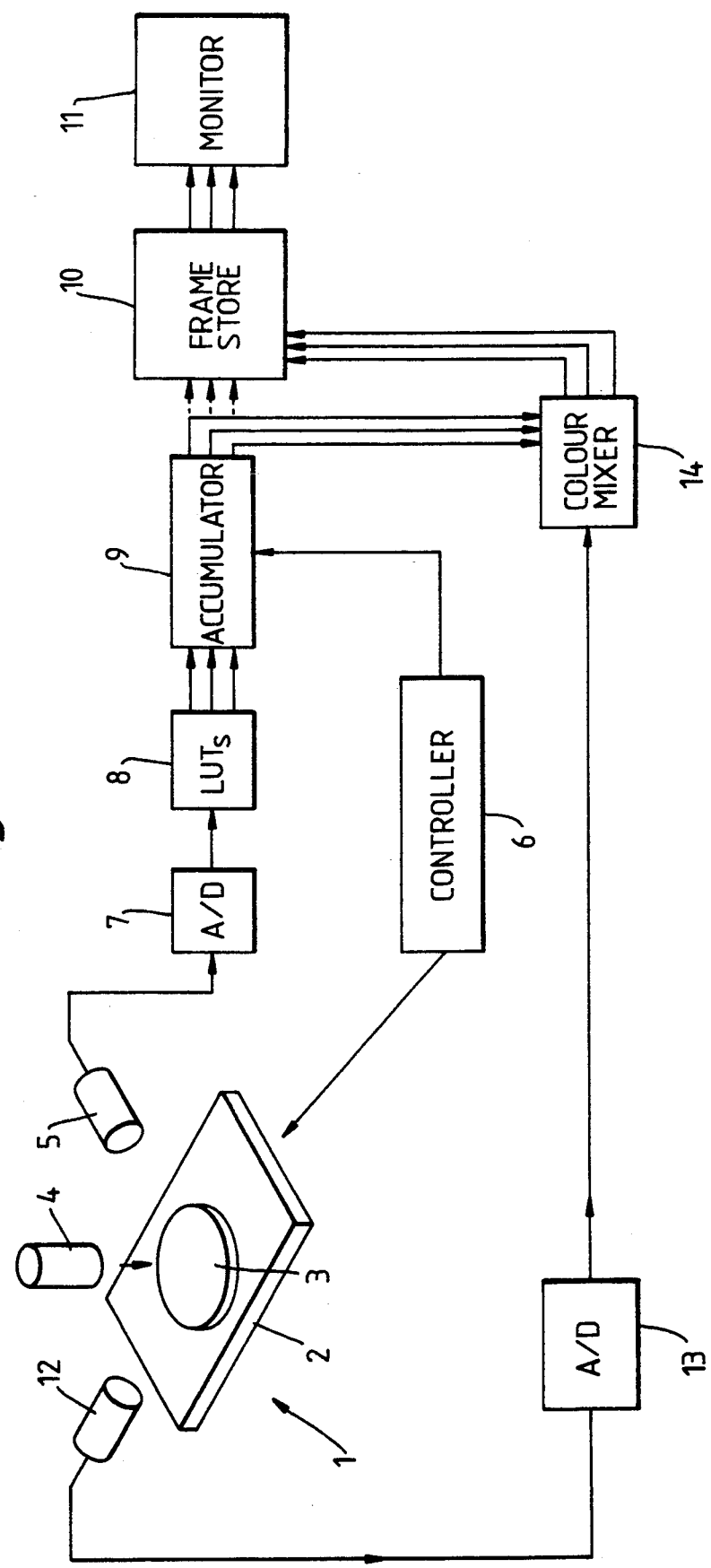
FIG. 1 is a block diagram of one example of the apparatus.

The apparatus shown in FIG. 1 comprises a conventional X-ray acquisition system 1 which is shown schematically in the drawing. Essentially, the system 1 includes a support 2 on which is provided a specimen 3. Above the specimen 3 is an electron beam source 4 while an energy dispersive X-ray detector 5 is positioned to receive X-rays or X-ray photons emitted by the specimen 3. A suitable detection system is the "Link eXL" or "Link ISIS" manufactured by Link Analytical Limited. The components so far described would normally be housed in a vacuum chamber (not shown). The electron beam source 4 can be deflected, alternatively, the support 2 can be moved relative to the electron beam, so that the beam scans the specimen 3. Typically, the scan would be an orthogonal raster scan achieved under the control of a controller 6.

The detector 5 outputs analogue signals which depend upon the energies of incoming X-ray photons. In this case, the detector 5 detects individual photons so that the output signal will represent the energy of each individual photon in sequence as it is received. However, coarser resolution detectors could also be used which generate a series of output signals, where each signal represents the average intensity of x-rays received within a particular range of energies during the dwell time while the electron beam from the source 4 impinges on a particular pixel position on the specimen 3. This will be described later.

Figure 2A:
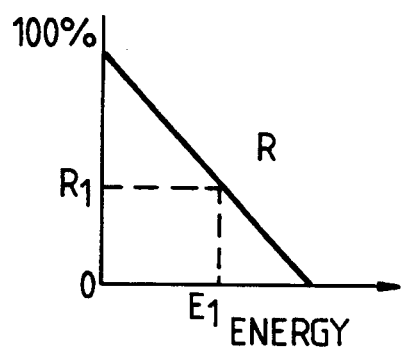
FIGS. 2A, 2B and 2C illustrate one example of a set of look-up tables.
Figure 2B:
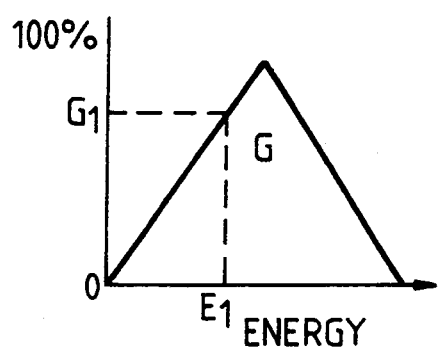
Figure 2C:
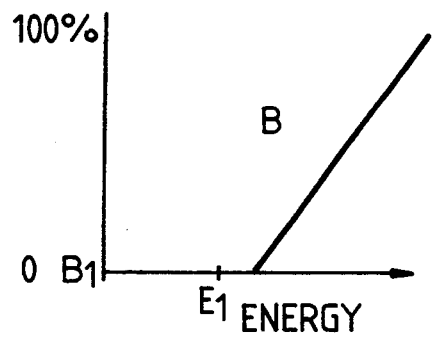

Each photon measurement signal from the detector 5 is digitised in an analogue-to-digital converter 7 and the resultant, digitised signal fed to a group of three look-up tables LUTs 8 which convert the energy into three visual colour component values red (R), green (G) and blue (B). The content of a suitable set of the LUTs 8 is shown in FIGS. 2A, 2B and 2C. A separate LUT is provided for each of the three colour components red, green, and blue and for example if the incoming value represents an energy of $E_1$ then the output data values from the LUTs 8 will have the values $R_1$, $G_1$, $B_1$.

In general the LUTs 8 should be loaded with functions which achieve the following:

1. All chemical elements should contribute to the image, not just selected elements. The LUTs should therefore span enough energy to include characteristic lines from every element. For example, 0–10 keV would be suitable.

2. Different photon energies should be converted to different colours and the R.G.B. components of each colour summed to get the overall colour for the spectrum. (This is quite different to converting the total number of photons to a single colour as in false colour methods where different total numbers give different colours). Further, for any energy value, preferably $R+G+B=$ constant, so that energy is converted to chromaticity rather than luminance.

3. Different compounds should exhibit different colours. With a fixed LUT operating over a fixed energy band, as shown in the example, these colours are objective and can be learned by the operator thus aiding recognition when new samples are viewed.

4. No operator intervention should be required to collect colour images. Set-up should be predetermined and objective so that different operators will produce images with similar colours from the same sample.

Figure 3A:
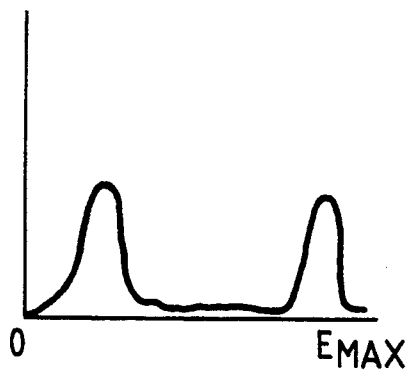
FIGS. 3A and 3B illustrate two different energy distributions for display.
Figure 3B:
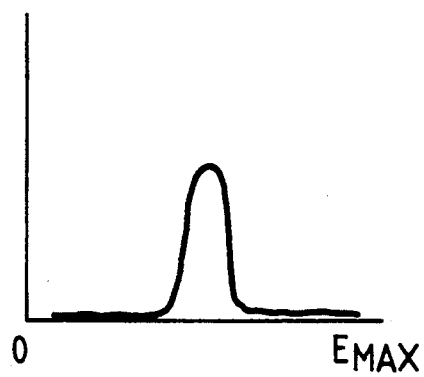

Given the requirements, the example LUTs shown in FIG. 2 exhibit the desirable properties:

a) The "rainbow" transition from red to blue is well known and provides the operator with a memorable indication of spectral distributions where a single energy dominates (i.e. if red, then predominantly low energies, if blue high energies etc).

b) If a uniform spectrum is presented to the LUT, the R,G,B values will be equal and "white" light is generated. This conforms to the concept of "white" radiation where all energies are equally represented.

c) Even if the mean energy of a spectral distribution is the same for two samples, the colour will be different provided the distribution of characteristic lines is different. For example, a spectrum with low energy (red) and high energy (blue) lines would give a magenta colour whereas another spectrum with a single midenergy line (green) would give a green colour even though it may have the same mean energy.

d) A distribution of energies as shown in FIG. 3A will lead to strong "R" and "B" results in the accumulator and therefore a "magenta" colour, whereas a distribution of energies as shown in FIG. 3B will lead to a strong "G" result in the accumulator and therefore a "green" colour.

Thus, even though the distributions have roughly the same mean energy, they can be distinguished on the basis of colour. By the conversion to colour, some of the spectral energy distribution information is encoded into the colour. Detection systems which only produce a single value cannot convert any spectral energy distribution information into colour.

After each energy signal has been converted to a set of three colour components, the output colour component values from the LUTs 8 are fed to an accumulator 9 which sums them with the corresponding R, G and B values respectively received since the start of the dwell time for the current pixel to generate final R, G, B values for this pixel. As the detector 5 is measuring individual photon energies, this accumulator 9 adds up the results for every photon that arrives while the electron beam dwells at this pixel position on the specimen 3. Thus, at the end of the dwell time for a pixel, the accumulator 9 will hold three totals for R, G and B which are used to represent the colour component densities which will be used for display of that pixel.

While the electron beam from the source 4 continues to irradiate the same pixel in the specimen 3, further X-ray energies are detected and fed to the LUTs 8 and further combinations of colour components generated. Each new set of colour component values is accumulated (summed) in the accumulator 9 until the controller 6 indicates that the electron beam is to be switched to the next pixel. In the simplest example the accumulated values are then downloaded directly to a frame store 10 where (possibly after scaling) they are stored in the location in the frame store 10 corresponding to the irradiated pixel. Alternatively, the accumulator results are added to the R.G.B. results already saved for the pixel in the frame store from previous scans over the image. In this case, the frame store provides additional signal averaging for multiple scans over the field of view. Once stored in the frame store, the colour component values control the display of an image of the pixel on a monitor 11 in a conventional manner. Conventional scaling and quantisation removal techniques may be required so that the display system provides an optimal representation of the colour described by the colour component values in the frame store.

Typically, the dwell time per pixel will be about 1 millisecond although with the best detectors currently available, this could be reduced to 100 microseconds thus providing a very quick scan of the specimen.

Figure 4:
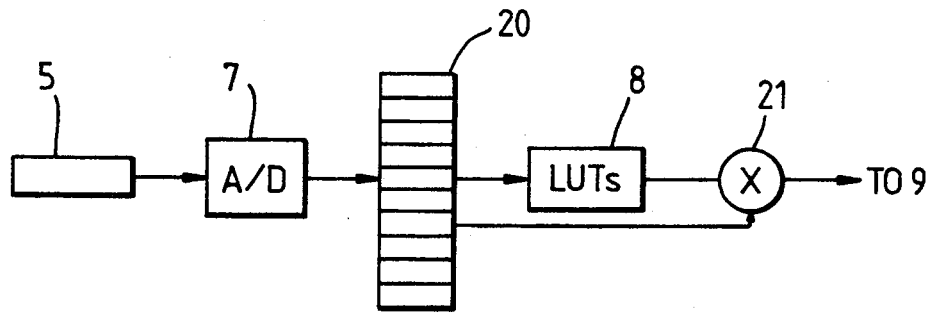
FIG. 4 is a block diagram of a first modified form of the initial processing components of the apparatus shown in FIG. 1.

In the system described in connection with FIG. 1, the detector 5 is a single detector which can detect individual photons and output signals representing the energy of those individual photons, those energy signals being fed directly to the LUTs 8 for conversion to R,G,B colour components. FIG. 4 illustrates an alternative configuration in which the output signals from the A/D convertor 7 are fed to a set of accumulators 20 (for example 32) each of which is associated with the respective band of X-ray energies. Each accumulator is incremented when a photon with an energy falling within the corresponding energy band determined by the A/D result is detected. At the end of the pixel dwell time, the accumulators 20 will hold values defining the total numbers of photons received in each energy band for that pixel. Then, for each energy band, the controller 6 causes the accumulators 20 to be down loaded in sequence to a multiplier 21 while at the same time a mean energy value for the energy band is fed to the LUTs 8. The resulting set of colour component signals R,G,B from the LUTs 8 are then multiplied by the value from the accumulator 20 by the multiplier 21 and the resultant, modified colour components are then fed to the accumulator 9.

Figure 5:
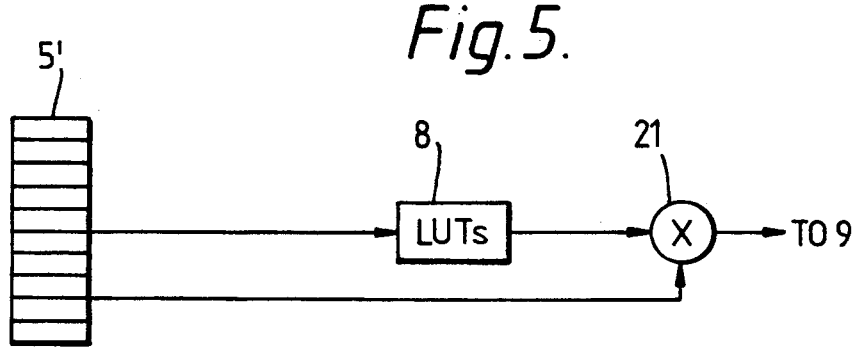
FIG. 5 is a second modified version of the initial processing components of the example shown in FIG. 1; and, FIG. 6 is a third modified example of the initial processing components shown in FIG. 1.

FIG. 5 illustrates a further alternative in which the detector 5 is replaced by a multi-segment detector 5' (for example a CCD array) which not only detects photons but stores a signal proportional to the number of photons received in each element. A dispersive element, such as curved "Bragg" reflecting crystal, (not shown), can be used as a "prism" to direct photons of different energy on to different segments of the multi-segment detector. Thus, the different segments will store signals proportional to the number of photons received in each of a number of energy bands in a similar way to the accumulator 20 of FIG. 4. These counts are then down loaded in sequence to the multiplier 21 while signals defining the mean energy level of the corresponding energy band are fed to the LUTs 8 which generates R,G,B values which are multiplied in the multiplier 21 as in FIG. 4.

Figure 6:
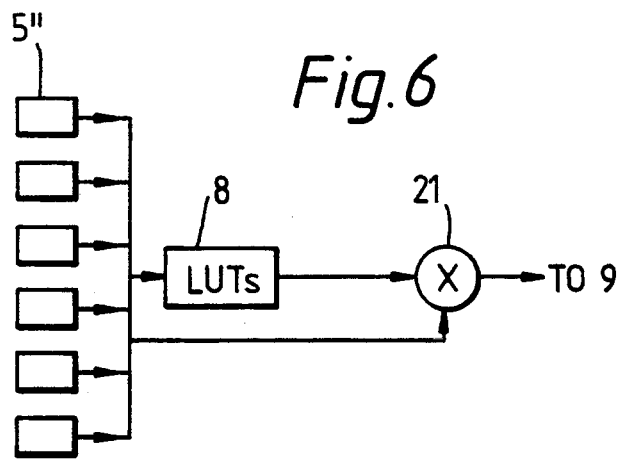

FIG. 6 illustrates a further alternative in which the detector 5 is replaced by a set of individual detectors 5", for example Bragg Crystal Spectrometers which are responsive to photons in respective energy bands and generate signals from corresponding counters constituting the number of photons received in the energy band concerned. These signals are fed to the multiplier 21 while the mean energy level for the energy band in question is fed to the LUTs 8 as in the FIG. 5 example.

The various examples of the invention described can be further modified to obtain sophisticated display by detecting backscattered or secondary electrons using a conventional detector 12 whose output signal is fed to an A/D converter 13, the digital output of which is then fed to a colour mixer 14. The detector 12 could be a Link Tetra manufactured by Oxford Instruments, Microanalysis Group to detect backscattered electrons. The colour component signals R,G,B from the accumulator 9 are fed instead to the colour mixer 14 where they are modified, as will be explained below, the resultant colour component signals then being fed to the frame store 10.

Although the intensity or luminance information in the X-ray data is very noisy, the hue and saturation or chromaticity is often determined with much higher precision, as explained above. This is easy to see if we consider a spectrum from a pure element where most X-rays emerge with the characteristic X-ray energy for that element; although we may accumulate only a few photons in a small measurement interval so the statistical function ($N^{0.5}$) is large, photons of the same energy are converted to the same R, G, B result so the balance of R, G, B or hue is the same, however long the acquisition interval.

The detector 12 detects the intensity of the electron signal obtained from each pixel and this is used to control the luminance of the colour signal derived from the X-ray data which controls hue and saturation or chromaticity.

One way of combining the signals is to allow the operator to select how much of the colour signal is to be combined with the electron signal. A prescribed proportion, f, of the X-ray colour signal ($X_r$, $X_g$, $X_b$) is added to the electron signal ($E_r$, $E_g$, $E_b$) and the result scaled so that the luminance matches that for the electron signal. At one extreme, the original monochroms electron image is seen, at the other, the full colour information appropriate to the X-ray signal. If we consider the image divided into a grid of picture elements or "pixels", then at a given pixel, the above combination is described by the formula:

$$\text{Mix} = EB \cdot (f \cdot X + (1-f) \cdot E) / (f \cdot XB + (1-f) \cdot EB) \quad (1)$$

where X is a vector representing the x-ray-derived colour ($X_r$, $X_g$, $X_b$), E is a vector representing the electron signal ($E_r$, $E_g$, $E_b$, where $E_r = E_g = E_b$ as it is monochrome), XB and EB are the mean luminances for the two signals (e.g. $XB = (X_r + X_g + X_b)/3$) and f is the proportion of X-ray colour to include in the final mix.

An alternative method of colouring the electron signal is to use only the chrominance information derived from the X-ray signal to colour the image and maintain the same luminance as the electron signal:

$$\text{Mix} = (f \cdot (EB/XB) \cdot (X - XB) + \underline{E}) \quad (2)$$

Note that this is computationally easier as there is no scaling factor required in this combination. When $f=1$, the image will be the same as when $f=1$ in formula (1).

In order to achieve the requirement for constant luminance more elaborate formulae may be required to compensate for the different characteristics of the display system for R, G and B components (see "Principles of Television Reception" by W. Wharton and D. Howorth, pub. Sir Isaac Pitman & Sons Ltd, 1967). The above are just two examples of how "chromaticity" information obtained from X-ray spectral data could be combined with the electron signal in a form which is intuitive for the user and maintains a high resolution image. There is the obvious possibility of variations on this theme.

It should be noted that whereas using the SED signal (or a quadrant BSED "difference" signal) will show a topographic image, coloured according to chemical composition a quadrant BSED "sum" signal will show luminance dependant on the mean atomic number of the underlying material. The combination of a colour cue for spectral shape and an intensity cue for atomic number should segment the image effectively into discrete areas with different chemical composition.

Instead of a single frame store 10, where use is made of an additional electron signal, two frame stores could be used, one for storing the monochrome electron signal and one for storing the X-ray derived colour signal. The final mix could then be accomplished after reading out both stores.

It is expected that the overall system shown in FIG. 1 can achieve scanning at a rate greater than one ms per pixel. In general, the X-ray data would be obtained on a coarser grid than the electron image and the X-ray image would then be interpolated up in a conventional manner to the same resolution of the electron image before applying the colour mixer. In a further alternative, two separate scans of the specimen could be carried out, one for the electron image and one for the X-ray image and then the result combined.

The invention may be used with any X-ray detection system that, by whatever means, produces an output which gives some indication of the spectral energy distribution for emitted X-rays. A unique aspect of the invention is in the use of X-ray spectral energy information to, objectively, colour code a high resolution luminance signal.

I claim:

1. Apparatus for displaying a visual image of an X-ray response of a specimen, the apparatus comprising:

a source for exciting X-ray emissions from a specimen;

a detector for detecting X-ray photons emitted from an array of pixels defined by the specimen;

a visual colour component generating circuit for generating, for each pixel of said array of pixels, sets of visual colour component signals related to the energies of x-ray photons emitted from each pixel and detected by the detector, wherein the range of detected X-ray energies is mapped into a range of visual colours;

an accumulator circuit for combining the respective colour component signals for each pixel of said array of pixels into a single set of colour components for each pixel; and a display responsive to the colour component signals from the accumulator circuit to display an image defined by the colour components.

2. Apparatus according to claim 1, wherein the source for exciting X-ray emissions comprises a focused beam of electrons.

3. Apparatus according to claim 1, wherein the source for exciting X-ray emissions comprises a radiation beam which is scanned across the specimen in a step-wise manner so as to excite a response from discrete pixels.

4. Apparatus according to claim 1, wherein the detector detects individual photons and outputs signals representing the energy of each photon, the visual colour component generating circuit generating a set of colour component signals for each photon.

5. Apparatus according to claim 4, further comprising a second accumulator circuit including an accumulator for each of a number of X-ray energy bands, each accumulator storing, during the period for which a pixel of said array of pixels is scanned, the number of photons generated in the corresponding energy band, wherein the visual colour component generating circuit generates a set of colour component signals for each energy band scaled by the values stored in the respective accumulators.

6. Apparatus according to claim 1, wherein the detector generates, during the period for which a pixel of said array of pixels is scanned, the number of photons generated in each of a plurality of energy bands, wherein the visual colour component generating circuit generates a set of colour component signals for each energy band scaled by the number of photons generated in that energy band.

7. Apparatus according to claim 6, wherein the detector comprises a plurality of individual detectors, one for each energy band.

8. Apparatus according to claim 1, wherein the visual colour component generating circuit includes one or more look up tables (LUTs) which contain data defining the visual colour component control signal values corresponding to each X-ray energy value or mean X-ray energy band.

9. Apparatus according to claim 5, wherein the visual colour component generating circuit includes one or more look-up tables (LUTs) which contain data defining the visual colour component control signal values corresponding to each X-ray energy value or mean X-ray energy band and wherein the output from the one or more LUTs is fed to a multiplier where it is multiplied by a value defining the number of photons in the corresponding energy band.

10. Apparatus according to claim 1, further comprising an auxiliary detector for detecting another characteristic of the specimen; and a modifying circuit for modifying the colour component signals from the accumulator circuit so as to modify the luminance of each pixel of said array of pixels while leaving the hue and saturation substantially unchanged.

11. Apparatus according to claim 10, wherein the auxiliary detector detects one of backscattered electrons and secondary electrons emitted by the specimen.

12. Apparatus according to claim 11, wherein the colour component signals are generated in accordance with the formula:

$$\text{Mix} = EB \cdot (f \cdot \underline{X} + (1-f) \cdot \underline{E}) / (f \cdot XB + (1-f) \cdot EB)$$

where $\underline{X}$ is a vector representing the x-ray derived colour, $\underline{E}$ is a vector representing the electron signal, XB and EB are the mean luminances for the two signals and f is the proportion of X-ray colour to include in the final mix.

13. Apparatus according to claim 11, wherein the colour component signals are generated in accordance with the formula:

$$\text{Mix} = (f \cdot (EB)/XB) \cdot (\underline{X} - XB) + \underline{E}$$

where $\underline{X}$ is a vector representing the x-ray derived colour,

E is a vector representing the electron signal,

XB and EB are the mean luminances for two signals and f is the proportion of X-ray colour to include in the final mix.

14. A method for displaying a visual image of an X-ray response of a specimen, the method comprising the steps of:

exciting X-ray emissions from a specimen;

detecting X-ray photons emitted from an array of pixels defined by the specimen;

generating, for each pixel of said array of pixels, sets of visual colour component signals related to the energies of X-ray photons emitted from each pixel and detected by the detector wherein the range of detected X-ray energies is mapped into a range of visual colours;

combining the respective colour component signals for each pixel of said array of pixels into a single set of colour components for each pixel; and displaying an image defined by the resultant set of colour components.

15. A method according to claim 14, wherein the step of detecting comprises detecting individual photons and generating signals representing the energy of each photon, wherein a set of colour component signals is generated for each photon.

16. A method according to claim 15, further comprising the step of storing, during the period for which a pixel of said array of pixels is scanned, the number of photons generated in each of a number of X-ray energy bands, the visual colour component generating step comprising generating a set of colour component signals for each energy band scaled by the values stored for that energy band.

* * * * *